United States Patent [19]

Hirano et al.

[11] 3,981,903

[45] Sept. 21, 1976

[54] CYCLOPROPANE CARBOXYLIC ACID ESTERS

[75] Inventors: Masachika Hirano, Ashiya; Isao Ohno, Minoo; Yoshitoshi Okuno, Toyonaka; Osamu Magara, Osaka; Nobushige Itaya, Nishinomiya; Toshio Nishioka, Takarazuka; Toshio Mizutani; Nobuo Ohno, both of Toyonaka; Takashi Matsuo, Nishinomiya; Hisami Takeda, Takarazuka, all of Japan

[73] Assignee: Sumitomo Chemical Company, Limited, Osaka, Japan

[22] Filed: July 25, 1974

[21] Appl. No.: 491,637

[30] Foreign Application Priority Data

July 28, 1973 Japan.............................. 48-85223

[52] U.S. Cl............................. 260/468 H; 424/305
[51] Int. Cl.$^2$........................................ C07C 69/74
[58] Field of Search................................ 260/468 H

[56] References Cited
UNITED STATES PATENTS 3,683,005   8/1972   Soto et al........................... 260/468

FOREIGN PATENTS OR APPLICATIONS 2,326,007   1/1974   Germany

OTHER PUBLICATIONS

Farkas et al., Chem. Listy. 52, 688 (1958).

*Primary Examiner*—Jane S. Myers
*Attorney, Agent, or Firm*—Stevens, Davis, Miller & Mosher

[57] ABSTRACT

A new pyrethroidal pesticide containing as an active ingredient a pesticidally effective amount of novel cyclopropanecarboxylic acid esters represented by the formula,

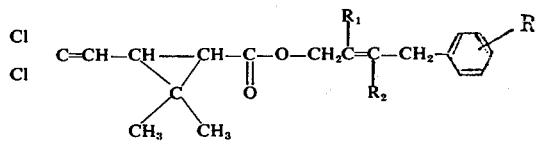

wherein R is a hydrogen atom, a halogen atom, a methyl or a methoxy group, and $R_1$ and $R_2$ are hydrogen atom, methyl group or a halogen atom, which have a low toxicity to mammals, excellent pesticidal effect on injurious pests in cereal storage, agriculture and forestry and a wide range of uses for prevention of epidemics.

6 Claims, No Drawings

CYCLOPROPANE CARBOXYLIC ACID ESTERS

This invention relates to novel cyclopropanecarboxylic acid esters represented by the general formula (I),

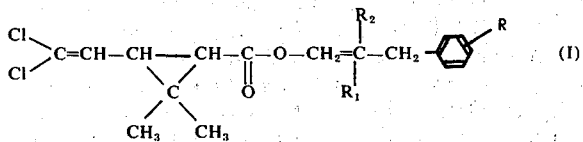

wherein R is a hydrogen atom, a halogen atom, a methyl or a methoxy group, and $R_1$ and $R_2$ are individually a hydrogen atom, a methyl group or a halogen atom, to processes for preparing said esters, and pesticides containing the same.

An object of the present invention is to provide at low costs pesticides for environment sanitation and for agriculture and horticulture which are low in toxicity to mammals and strong in miticidal and insecticidal effects.

Among pesticides available at present, those which are quick in knock down effect and are so harmless to mammals as to be safely usable are pyrethrum extracts (containing pyrethrins) and synthetic allethrins, which are homologues of active ingredients of said extracts. Despite of their being high in usefulness, however, the pyrethrum extracts and synthetic allethrins are relatively expensive and hence have such drawback as being restricted in application scope.

The present inventors synthesized various cyclopropanecarboxylic acid esters and investigated the biological activities of said esters. As a result, the inventors found that the esters represented by the aforesaid general formula (I) are not only so excellent in pesticidal activities as to successfully control sanitary injurious insects such as houseflies, agriculture injurious insects such as green rice leafhoppers, diamondback moths and cutworms, and various mites, but also are low in toxicity to mammals and can be prepared at low costs. Based on the above finding, the inventors have accomplished the present invention.

While the pesticides of the present invention find broad uses for the prevention of epidemics, they display prominent pesticidal activities against pests injurious to stored cereals, agriculture and forestry, and hence are quite useful for the control of said injurious pests. Particularly because of their being low in toxicity, the pesticides are applicable to crops before harvest and food-packaging materials and usable for green house cultivation and house horticulture.

The cyclopropanecarboxylic acid esters represented by the general formula (I) are novel esters which have first been synthesized by the present inventors. The said esters can be obtained by reacting an alcohol, or a reactive derivative thereof, represented by the general formula (II),

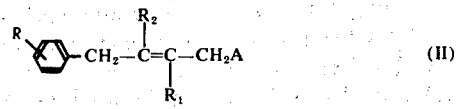

wherein R, $R_1$ and $R_2$ are as defined previously, and A is a hydroxy group, a halogen atom or an arylsulfoxy group, with cyclopropanecarboxylic acid represented by the formula (III),

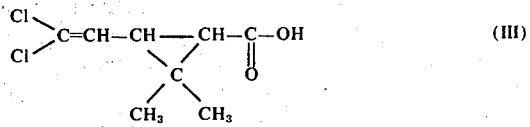

or a reactive derivative thereof, if necessary in the presence of a suitable solvent, reaction auxiliary reagent or catalyst.

The reactive derivative of the alcohol of the formula (II) includes compounds formed by substituting the hydroxy group of the alcohol with a halogen atom or a tosyloxy group, and the reactive derivative of the cyclopropanecarboxylic acid of the formula (III) includes acid halides, acid anhydrides and alkali metal salts.

The esters represented by the formula (I) include geometrical isomers derived from the steric structure of the carboxylic acid (III) and optical isomers derived from asymmetric carbon atoms of the alcohol (II) and the carboxylic acid (III), and it is undouted to say that these isomers are also involved in the scope of the present invention.

Processes for preparing the esters represented by the formula (I) are explained in more detail below.

1. Process in which the ester of the formula (I) is obtained by reacting the alcohol of the formula (II) with the carboxylic acid of the formula (III) or its acid halide, or acid anhydride:

In case the acid itself is used, the reaction can be accomplished under dehydration conditions. That is, the ester of the formula (I) can be obtained by reacting the alcohol of the formula (II) with the carboxylic acid of the formula (III) at an elevated temperature in the presence of an acid catalyst such as mineral acid or p-toluenesulfonic acid and of an azeotropic solvent such as benzene or toluene. Alternatively, the present compound can be obtained by reacting the alcohol with the carboxylic acid at or above room temperature in an inert solvent such as benzene or petroleum ether in the presence of a dehydrating agent such as dicyclohexylcarbodiimide.

In case a halide of the carboxylic acid is used, the reaction can be sufficiently accomplished at room temperature by reacting the halide with the alcohol of the formula (II) using as a dehydrohalogenating agent an organic tertiary base such as pyridine or triethylamine. The acid halide used in this case may be any of the halides within the scope of the present invention, but is ordinarily an acid chloride. In the reaction, the use of a solvent is desirable for smooth progress of the reaction, and an inert solvent such as benzene, toluene or petroleum benzine is ordinarily used.

In case an anhydride of the carboxylic acid is used, no auxiliary agent is particularly required, and the present compound can be obtained by reacting the acid anhydride with the alcohol of the formula (II). In this case, the elevation of temperature is preferable for acceleration of the reaction, and the use of an inert solvent is preferable for smooth progress of the reaction, though these are not always indispensable.

2. Process in which the ester of the formula (I) is obtained by use of a compound formed by substituting with a halogen atom the hydroxy group of the alcohol of the formula (II):

The halogen atom in this case is ordinarily a chlorine or bromine atom, but may be any of other halogen atoms. The carboxylic acid of the formula (III), which is the other reactant, may be used in the form of an alkali metal salt or a salt of an organic tertiary base, or a base capable of forming said salt may be added at the time of reaction together with the carboxylic acid. In this process, it is desirable for smooth progress of the reaction to use an inert solvent such as benzene or acetone and to elevate the temperature to or below the boiling point of the solvent.

3. Process in which the ester of the formula (I) is obtained by use of a compound represented by the general formula (IV),

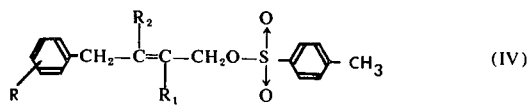

wherein R, $R_1$ and $R_2$ are as defined previously, which is formed by substituting with a tosyloxy group the hyroxy group of the alcohol of the formula (II):

In this process, the form of the other reactant and the reaction conditions are same as in the case of the process (2).

The carboxylic acid of the formula (III), which is used in the process of the present invention, has been disclosed by J. Farkas et al.: Chem. Listy., 52 688 (1958) [C. A., 52 13650 (1958)] and reported to be such that the effect thereof as an allethrolon ester is close to that of a chrysanthemic acid ester. The said acid can easily be obtained from such inexpensive materials as chloral and isobutene. The reactive derivatives of the carboxylic acid can be easily derived from the acid according to known methods, e.g. methods applied to chrysanthemum-monocarboxylic acid.

The alcohol of the formula (II), which is used in the process of the present invention, can easily be obtained, for example, by reaction of the compound of the formula,

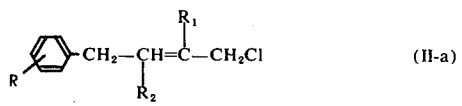

wherein R, $R_1$ and $R_2$ are the same as defined previously, and potassium p-nitrobenzoate, further recrystallizing and then hydrolyzing the obtained ester. The preparation of a part of the compound of the formula (II-a) has been disclosed in C. A. 60, 14410 (1964).

The compound formed by substituting the hydroxy group of the alcohol of the formula (II) with a halogen atom or a tosyloxy group can be easily obtained by halogenating the alcohol of the formula (II) or reacting p-toluenesulfochloride with said alcohol.

The processes of the present invention are illustrated below with reference to examples.

In the first place, standard processes of the invention are explained below.

A. Process according to the reaction of alcohol with carboxylic acid halide:

A solution of 0.05 mole of the alcohol in 3 times the volume thereof of dry benzene was incorporated with 0.075 mole of pyridine. To this solution was added a solution of 0.053 mole of carboxylic acid chloride in 3 times the volume thereof of dry benzene, whereby an exothermic reaction took place. The mixed solution was allowed to stand overnight in a tightly sealed vessel to deposit a pyridine hydrochloride precipitate. Thereafter, a small amount of water was added to the solution to dissolve the pyridine hydrochloride precipitate, and the aqueous layer was separated. The organic layer was successively washed with a 5 % aqueous hydrochloric acid solution, a saturated aqueous sodium hydrogencarbonate solution and a saturated aqueous sodium chloride solution, dried over anhydrous sodium sulfate and then freed from benzene by distillation, and the residue was purified according to silica gel chromatography to obtain the desired ester.

B. Process according to the dehydration reaction of alcohol with carboxylic acid:

A solution of 0.05 mole of the alcohol in 3 times the volume thereof of benzene was mixed with a solution of 0.05 mole of the carboxylic acid in 3 times the volume thereof of benzene. The mixed solution was incorporated with 0.08 mole of dicyclohexylcarbodiimide and then allowed to stand overnight in a tightly sealed vessel. On the next day, the solution was refluxed for 2 hours to terminate the reaction. Thereafter, the same after-treatment as in the standard process A to obtain the desired ester.

C. Process according to the reaction of alcohol with carboxylic acid anhydride:

A solution of 0.05 mole of the alcohol in 3 times the volume thereof of toluene was mixed with 0.05 mole of a carboxylic anhydride (synthesized from the carboxylic acid and acetic anhydride), and the resulting mixture was heated at 100°C. for 3 hours. After cooling to below 10°C., the mixture was neutralized by addition of a 10 % aqueous sodium hydroxide solution, and carboxylic acid formed by the reaction was recovered as a sodium salt. Subsequently, the organic layer was subjected to the same after-treatment as in the standard process A to obtain the desired ester.

D. Process according to the reaction of methyl halide with carboxylic acid:

A solution of 0.05 mole of a methyl halide and 0.06 mole of the carboxylic acid in 3 times the volume of the two of acetone was heated to and maintained at 15° to 20°C. Into the solution was gradually dropped with stirring a solution of 0.08 mole of triethylamine in 3 times the volume thereof of acetone. After completion of the dropping, the mixed solution was refluxed 2 hours to terminate the reaction. After cooling, the reaction liquid was separated from deposited triethylamine hydrochloride by filtration, and the filtrate was freed from acetone by distillation. To the residue was added 3 times the volume thereof of benzene, and the resulting mixture was subjected to the same aftertreatment as in the standard process A to obtain the desired ester.

E. Process according to the reaction of arylsulfonate of alcohol with carboxylic acid salt:

To a solution of 0.05 mole of tosylate of the alcohol in 3 times the volume thereof of acetone was gradually added with thorough stirring at room temperature 0.06 mole of sodium carboxylate (synthesized by reacting the carboxylic acid in water with an equimolar amount of sodium hydroxide, and then removing the water by distillation to dryness), and the resulting mixture was refluxed for 30 minutes to terminate the reaction. After cooling, the reaction mixture was separated from deposited solids by filtration, and the filtrate was freed from acetone by distillation. The residue was dissolved in 3 times the volume thereof of benzene, and the resulting solution was subjected to the same aftertreatment as in the standard process A to obtain the desired ester.

Several esters obtained according to the abovementioned standard processes are shown in the table below, but it is of course that the compounds of the present invention are not limited only to these. In the column "Elementary analysis" of the table, (C) is the abbreviation of "Calculated", and (F) "Found".

tion are shown below with reference to test examples. The other compounds of the invention also display similar effects.

TEST EXAMPLE 1

Pesticidal effect on green rice leafhoppers

The present compounds (1), (2), (3), (4), (5) and (6) were individually formulated according to ordinary procedure into 20 % emulsifiable concentrates. As a

| Run No. | Alcohol or its derivative | Carboxylic acid or its derivative | Reaction process | Compound No. | Compound name | Yield (%) | Refractive index ($n_D^{25}$) | Elementary analysis C (%) | H (%) |
|---|---|---|---|---|---|---|---|---|---|
| 1 | 3-Chloro-4-phenyl-trans-2-butene-1-ol | Acid chloride | A | (1) | 3-Chloro-4-phenyl-trans-2-butene-1-yl 2',2'-dimethyl-3'-(2'',2''-dichlorovinyl)-cyclopropanecarboxylate | 94 | 1.5481 | (F) 57.63 (C) 57.85 (for $C_{18}H_{19}O_2Cl_3$) | 5.32 5.12 |
| 2 | 3-Bromo-4-phenyl trans-2-butene-1-ol | Acid chloride | A | (2) | 3-Bromo-4-phenyl-trans-2-butene-1-yl 2',2'-dimethyl-3'-(2'',2''-dichlorovinyl)-cyclopropanecarboxylate | 94 | 1.5563 | (F) 51.55 (C) 51.70 (for $C_{18}H_{19}O_2Cl_2Br$) | 4.63 4.58 |
| 3 | 4-Phenyl-trans-2-butene-1-ol | Acid chloride | A | (3) | 4-Phenyl-trans-2-butene-1-yl 2',2'-dimethyl-3'-(2'',2''-dichlorovinyl)-cyclopropanecarboxylate | 93 | 1.5377 | (F) 63.77 (C) 63.91 (for $C_{18}H_{20}O_2Cl_2$) | 5.71 5.96 |
| 4 | 3-Methyl-4-phenyl-2-butene-1-yl chloride | Sodium carboxylate | D | (4) | 3-Methyl-4-phenyl-2-butene-1-yl 2',2'-dimethyl-3'-(2'',2''-dichlorovinyl)-cyclopropanecarboxylate | 81 | 1.5396 | (F) 64.93 (C) 64.78 (for $C_{19}H_{22}O_2Cl_2$) | 6.36 6.29 |
| 5 | 3-Chloro-4-phenyl-trans-2-butene-1-yl chloride | Potassium salt of d-trans acid | D | (5) | 3-Chloro-4-phenyl-trans-2-butene-1-yl d-trans-2',2'-dimethyl-3'-(2'',2''-dichlorovinyl)-cyclopropanecarboxylate | 84 | 1.5465 | (F) 57.61 (C) 57.85 (for $C_{18}H_{19}O_2Cl_3$) | 5.43 5.12 |
| 6 | 2,3-Dichloro-4-phenyl-trans-2-butene-1-yl chloride | Potassium salt of acid | D | (6) | 2,3-Dichloro-4-phenyl-trans-2-butene-1-yl 2',2'-dimethyl-3'-(2'',2''-dichlorovinyl)-cyclopropanecarboxylate | 81 | 1.5558 | (F) 53.32 (C) 52.97 (for $C_{18}H_{18}O_2Cl_4$) | 4.61 4.45 |
| 7 | 2,3-Dimethyl-4-phenyl-trans-2-butene-1-yl chloride | Potassium salt of acid | D | (7) | 2,3-Dimethyl-4-phenyl-trans-2-butene-1-yl 2',2'-dimethyl-3'-(2'',2''-dichlorovinyl)-cyclopropanecarboxylate | 65 | 1.5332 | (F) 65.25 (C) 65.40 (for $C_{20}H_{24}O_2Cl_2$) | 6.44 6.59 |
| 8 | 3-Chloro-4-(p-tolyl)-trans-2-butene-1-yl chloride | Potassium salt of acid | D | (8) | 3-Chloro-4-(p-tolyl)-trans-2-butene-1-yl 2',2'-dimethyl-3'-(2'',2''-dichlorovinyl)-cyclopropanecarboxylate | 86 | 1.5429 | (F) 58.76 (C) 58.85 (for $C_{19}H_{21}O_2Cl_3$) | 5.54 5.46 |
| 9 | 3-Chloro-4-(p-fluorophenyl)-2-butene-1-yl chloride | Potassium salt of acid | D | (9) | 3-Chloro-4-(p-fluorophenyl)-2-butene-1-yl 2',2'-dimethyl-3'-(2'',2''-dichlorovinyl)-cyclopropanecarboxylate | 83 | 1.5344 | (F) 55.38 (C) 55.19 (for $C_{18}H_{18}O_2FCl_3$) | 4.91 4.63 |
| 10 | 3-Chloro-4-(o-fluorophenyl)-2-butene-1-yl chloride | Potassium salt of acid | D | (10) | 3-Chloro-4-(o-fluorophenyl)-2-butene-1-yl 2',2'-dimethyl-3'-(2'',2''-dichlorovinyl)-cyclopropanecarboxylate | 82 | 1.5377 | (F) 56.26 (C) 56.52 (for $C_{18}H_{18}O_2FCl_3$) | 5.31 5.24 |
| 11 | 3-Chloro-4-(p-methoxyphenyl)-2-butene-1-yl chloride | Potassium salt of acid | D | (11) | 3-Chloro-4-(p-methoxyphenyl)-2-butene-1-yl 2',2'-dimethyl-3'-(2'',2''-dichlorovinyl)-cyclopropanecarboxylate | 82 | 1.5487 | (F) 56.26 (C) 56.52 (for $C_{19}H_{21}O_3Cl_3$) | 5.31 5.24 |

In order to further clarify the fact that the compounds of the present invention have excellent effects, insecticidal effects of typical compounds of the invention standard compound, 3,4-dimethylphenyl-N-methyl carbamate [hereinafter referred to as "Meobal" (registered trademark of Sumitomo Chemical Co., Ltd.)]

was also formulated into a 20 % emulsifiable concentrate.

In flower pots of 9 cm. in diameter, about 20 rice seedlings per pot were grown to the stage of 3 to 4 leaves. Each of the above-mentioned emulsifiable concentrates was diluted with water to 200 times, and sprayed to the seedlings by use of a turn table. After air-drying, the seedlings were put in a 5 liter glass beaker, which was then covered at the top with gauze. Thereafter, 20 green rice leafhoppers were liberated into the beaker, and the number of knocked down insects was counted with lapse of time to calculate the value of $KT_{50}$ (50 % knock-down time). On the next day, the number of dead and alive insects was counted to calculate the mortality. The results obtained were as set forth in Table 1.

Table 1

| Test compound | | $KT_{50}$ (min) | Mortality (%) |
|---|---|---|---|
| Present compound | (1) | 19' | 100 |
| " | (2) | 13' | 100 |
| " | (3) | 11' | 100 |
| " | (4) | 15' | 100 |
| " | (5) | 9' | 100 |
| " | (6) | 21' | 100 |
| Meobal | | 24' | 100 |

TEST EXAMPLE 2

Pesticidal effects on diamondback moths

The present compounds (1), (2), (3) and (4) were individually formulated according to ordinary procedure into 20 % emulsifiable concentrates. As a control, DDVP was also formulated into a 20 % emulsifiable concentrate.

Each of the above-mentioned emulsifiable concentrates was diluted with water to a test concentration, and 10 ml. of the resulting dilution was sprayed to the potted Chinese cabbages at the stage of 3 to 4 leaves. Subsequently, the cabbage leaves were put in a glass Petri dish of 14 cm. in diameter and 7 cm. in height, and 10 diamondback moth larvae at the fourth instar stage were liberated into the dish. After 2 days, the number of dead and alive larvae was counted to calculate the value of $LC_{50}$ (50 % lethal concentration). The results obtained were as set forth in Table 2.

Table 2

| Test compound | | $LC_{50}$ (p.p.m.) | Ratio of effect |
|---|---|---|---|
| Present compound | (1) | 43 | 8.6 |
| " | (2) | 56 | 6.6 |
| " | (3) | 48 | 7.7 |
| " | (4) | 75 | 4.9 |
| DDVP | | 370 | Defined as 1.0 |

DDVP: 0,0-Dimethyl 0-2,2-dichlorovinyl phosphate

TEST EXAMPLE 3

Pesticidal effects on housefly adults dl-Trans isomers of the present compounds (1), (2), (3) and (4) were individually formulated by use of deodorized kerosene into 0.2 % oil preparations. As a control, pyrethrin was also formulated into a 0.2 % oil preparation.

Using the Campbell's turn table [Soap and Sanitary Chemicals; Vol. 14, No. 119 (1938)], 5 ml. of each of the above-mentioned oil preparations was sprayed. When 20 seconds had elapsed after the spraying, the shutter was opened, and a group of about 100 housefly adults were exposed to the settling mist for 10 minutes. Subsequently, the number of knocked down houseflies was counted to calculate the knock-down ratio. The houseflies were then transferred to another cage, fed and allowed to stand for a day at room temperature. Thereafter, the number of dead and alive houseflies was counted to calculate the mortality. The results obtained were as set forth in Table 3.

Table 3

| Test compound | | Ratio of knocked down houseflies after 10 minutes (%) | Mortality (%) |
|---|---|---|---|
| Present compound | (1) | 100 | 100 |
| " | (2) | 100 | 99 |
| " | (3) | 100 | 100 |
| " | (4) | 100 | 98 |
| Pyrethrin | | 100 | 44 |

Because of their having such prominent effects as mentioned above, the pesticides of the present invention find wide uses for the prevention of epidemics by killing flies, mosquitoes and cockroaches, and for the control of common grain mites, Indian meal moths, rice weevils and the like pests injurious to stored cereals. Furthermore, they are markedly effective not only for the control of agriculture, horticulture and forestry injurious pests such as planthoppers, leafhoppers, armyworms, tortrixes, aphids, stem borers, spider mites and chestnut aphids, but also for the control of lice and ticks parasitic to animals, and many other injurious pests.

The pesticides of the present invention can not only knock down and kill the injurious insects but also have such effects as to evade hosts from pests. Particularly, the pesticides are low in toxicity and harmless to mammals, and hence are quite advantageous in that they are freely applicable to crops before harvest and food-packaging materials and are safely usable for house horticulture and green house cultivation.

In actual application, the present compounds can be used singly without addition of any other component, or, for easier application as controlling chemicals, may be used in admixture with carriers. The compounds may be formulated, according to procedures thoroughly known to those skilled in the art, into optional forms such as emulsifiable concentrates, wettable powders, dusts, granules, fine granules, oil sprays, aerosols, heating fumigants (e.g. mosquito coils, electric mosquito killer mat, etc.), fogging mists, non-heating fumigants and poisonous baits, and may be put into various uses by shaping the compounds into desired forms by use of carriers.

The present compounds can be enhanced in insecticidal effect when used in admixture with synergists for pyrethroides such as α-[2-(2-butoxyethoxy)ethoxy]-4,5-methylenedioxy-2-propyltoluene (hereinafter referred to as "Piperonyl butoxide"), 1,2-methylenedioxy-4-[2-(octylsulfinyl)propyl]benzene (hereinafter referred to as "Sulfoxide"), 4-(3,4-methylenedioxyphenyl)-5-methyl-1,3-dioxane (hereinafter referred to as "Sufroxane"), N-(2-ethylhexyl)-bicyclo(2,2,1)hepta-5-ene-2,3-dicarboximide (hereinafter referred to as "MGK-264"), octachlorodipropyl ether (hereinafter referred to as "S-421") and isobornyl thiocyanoacetate (hereinafter referred to as "Thanite"), or with other known synergists effective for allethrin and pyrethrin.

Generally, chrysanthemic acid ester type compounds are low in stability to light, heat and oxidation. Accordingly, when antioxidants or ultraviolet absorbers, e.g. phenol derivatives such as BHT and BHA, bisphenol derivatives, arylamines such as phenyl-α-naphthylamine, pheyl-β-naphthylamine and phenetidineacetone condensates or benzophenone type compounds are added in suitable amounts as stabilizers, it is possible to obtain pesticidal compositions which have been more stabilized in effectiveness.

Furthermore, the present compounds may be used in admixture with other physiologically active materials, e.g. other known cyclopropanecarboxylic acid ester type insecticides such as allethrin, N-(chrysanthemoxymethyl)-3,4,5,6-tetrahydrophthalimide (hereinafter referred to as "Tetramethrin"), 5-benzyl-3-furylmethyl chrysanthemate [hereinafter referred to as "Chrysron" (registered trademark of Sumitomo Chemical Co., Ltd.)], 3-phenoxybenzyl chrysanthemate, 5-propargylfurfuryl chrysanthemate, 2-methyl-5-propargyl-3-furylmethyl chrysanthemte and their d-trans-chrysanthemic acid esters or d-cis-trans-chrysanthemic acid esters, pyrethrum extracts, or d-trans-chrysanthemic acid or d-cis-trans-chrysanthemic acid esters of d-allethrolon and the like; organo-chlorine type insecticides such as DDT, BHC, Methoxychlor and the like; organo-phosphorus type insecticides such as O,O-dimethyl-O-(3-methyl-4-nitrophenyl)phosphorothioate [hereinafter referred to as "Sumithion" (registered trademark of Sumitomo Chemical Co., Ltd.)], O,O-dimethyl-O-4-cyanophenyl phosphorothioate [hereinafter referred to as "Cyanox" (registered trademark of Sumitomo Chemical Co., Ltd.)], O,O-dimethyl-O-(2,2-dichlorovinyl) phosphate (hereinafter referred to as "DDVP") and the like; carbamate type insecticides such as 1-naphthyl-N-methyl carbamate, 3,4-dimethylphenyl-N-methyl carbamate [hereinafter referred to as "Meobal" (registered trademark of Sumitomo Chemical Co., Ltd.] and the like or the other insecticides, or with other agricultural chemicals such as fungicides, nematocides, acaricides, herbicides, plant growth regulators, fertilizers, microbial pesticides such as BT preparations, BM preparations and the like, and insect hormones, whereby multi-purpose composition more enhanced in effectiveness can be prepared and synergistic effects due to blending therewith may be expected.

Formulation procedures and effects of the present pesticides are illustrated below with reference to Formulation Examples and Examples, in which all parts are by weight.

FORMULATION EXAMPLE 1

0.1 Part of d-trans-isomer of each of the present compounds (1), (2), (3), (4), (6), (7), (8), (9), (10) and (11) was dissolved in 99.9 parts of deodorized kerosene to obtain oil preparations of the respective compounds.

FORMULATION EXAMPLE 2

A mixture comprising 0.05 part of dl-trans-isomer of each of the present compounds (1), (2), (3), (4), (6), (7), (8), (9), (10) and (11), and 0.2 part of piperonyl butoxide was dissolved in 99.75 parts of deodorized kerosene to obtain oil preparations of the respective compounds.

FORMULATION EXAMPLE 3

A mixture comprising 20 parts of each of the present compounds (1), (2), (3), (4), (5), (6), (7), (8), (9), (10) and (11), 15 parts of Sorpol SM-200 (a surfactant produced by Toho Kagaku Co., Ltd.) and 5 parts of xylene was thoroughly stirred to obtain emulsifiable concentrates of the respective compounds.

FORMULATION EXAMPLE 4

A mixture comprising 10 parts of dl-trans-isomer of each of the present compounds (1), (2), (3), (4), (6), (7), (8), (9), (10) and (11), 20 parts of S-421, 15 parts of Sorpol SM-200 and 55 parts of xylene was thoroughly stirred to obtain emulsifiable concentrates of the respective compounds.

FORMULATION EXAMPLE 5

A mixture comprising 0.1 parts of dl-trans-isomer of the present compound (1), 0.2 part of tetramethrin, 7 parts of xylene and 7.7 parts of deodorized kerosene was charged in an aerosol container. After attaching a valve portion to the container, 85 parts of a propellant (liquefied petroleum gas) was filled under pressure through said valve portion into the container to obtain an aerosol preparation.

FORMULATION EXAMPLE 6

A mixture comprising 0.3 part of dl-trans-isomer of the present compound (3), 0.1 part of d-trans-chrysanthemic acid ester of Chrysron, 7 parts of xylene and 7.6 parts of deodorized kerosene was charged in an aerosol container. After attaching a valve portion to the container, 85 parts of a propellant (liquefied petroleum gas) was filled under pressure through said valve portion into the container to obtain an aerosol preparation.

FORMULATION EXAMPLE 7

A mixture comprising 0.2 part of d-trans-isomer of the present compound (4), 0.1 part of Chrysron, 7 parts of xylene and 7.7 parts of deodorized kerosene was charged in an aerosol container. After attaching a valve portion to the container, 85 parts of a propellant (liquefied petroleum gas) was filled under pressure through said valve portion into the container to obtain an aerosol preparation.

FORMULATION EXAMPLE 8

A solution in 20 ml. of methanol of a mixture comprising 0.3 g. of d-trans-isomer of each of the present compounds (1), (2), (3) and (4), 0.3 g. of allethrin and 0.6 g. of BHT was uniformly mixed under stirring with 98.8 g. of a mosquito coil carrier (a 3 : 5 : 1 mixture of Tabu powder, pyrethrum marc and wood flour). The resulting mixture, after evaporation of methanol, was sufficiently kneaded with 150 ml. of water, shaped and dried to obtain mosquito coils of the respective compounds.

FORMULATION EXAMPLE 9

A solution in 20 ml. of methanol of a mixture comprising 0.15 g. of dl-trans-isomer of each of the present compounds (1), (2), (3), (4), (6), (7), (8), (9), (10) and (11) and 0.2 g. of d-trans-isomer of allethrin was uniformly mixed under stirring with 99.65 g. of the same mosquito coil carrier as in Formulation Example 8. The resulting mixture, after evaporation of methanol, was sufficiently kneaded with 150 ml. of water, shaped and dried to obtain mosquito coils of the respective compounds.

FORMULATION EXAMPLE 10

A mixture comprising 0.1 g. of dl-trans-isomer of each of the present compounds (1) and (4), 0.1 g of BHT and 0.1 g. of piperonyl butoxide was dissolved in a proper amount of chloroform and uniformly adsorbed in a filter paper of 3.5 cm. × 1.5 cm. in area and 0.3 cm. in thickness to obtain fibrous fumigant compositions of the respective compounds capable of being used by heating on an electrically heated plate.

In addition to the filter paper, there may be used any other fibrous carrier such as a pulp or asbestos sheet which is equivalent in effectiveness to the filter paper.

FORMULATION EXAMPLE 11

A mixture comprising 0.02 g. of d-cis-trans-isomer of the present compound (4), 0.05 g. of 5-propargylfurfuryl-dl-cis-trans-chrysanthemate and 0.1 g. of BHT was dissolved in a proper amount of chloroform and uniformly adsorbed in a filter paper of 3.5 cm. × 1.5 cm. in area and 0.3 cm. in thickness to obtain a fibrous fumigant composition capable of being used by heating on an electrically heated plate.

FORMULATION EXAMPLE 12

A mixture comprising 20 parts of each of the present compounds (1) and (2), 10 parts of Sumithion and 5 parts of Sorpol SM-200 was sufficiently stirred in a mortar with 65 parts of 300 mesh talc to obtain wettable powder preparations of the respective compounds.

FORMULATION EXAMPLE 13

A solution in 20 parts of acetone of a mixture comprising 1 part of dl-trans-isomer of each of the present compounds (3) and (4) and 2 parts of 1-naphthyl-N-methyl carbamate was sufficiently stirred in a mortar with 97 parts of 300 mesh diatomaceous earth, and then acetone was removed by evaporation to obtain dust preparations of the respective compounds.

FORMULATION EXAMPLE 14

A mixture comprising 3 parts of dl-trans-isomer of each of the present compounds (1), (2), (3), (4), (6), (7), (8), (9), (10) and (11), and 5 parts of Toyolignin CT (registered trademark of Toyo Boseki Co.) was sufficiently stirred in a mortar with 92 parts of GSM Clay (registered trademark of Zieklite Kogyo Co.). The resulting mixture was kneaded with 10 % by weight of water, granulated by means of a granulator and then air-dried to obtain granule preparations of the respective compounds.

FORMULATION EXAMPLE 15

A mixture comprising 4 parts of each of the present compounds (1) and (2), 2 parts of Cyanox and 5 parts of Toyolignin CT was sufficiently stirred in a mortar with 89 parts of GSM Clay. The resulting mixture was kneaded with 10 % by weight of water, granulated by means of a granulator and then air-dried to obtain fine granule preparations of the respective compounds.

FORMULATION EXAMPLE 16

A mixture comprising 0.1 part of d-trans-isomer of the present compound (4), 0.2 part of d-trans-isomer of allethrin, 11.7 parts of deodorized kerosene and 1 part of an emulsifier Atmos 300 (registered trademark of Atlas Chemical Co.) was emulsified with 50 parts of pure water. The resulting emulsion was filled together with 35 parts of a 3 : 1 mixture of deodorized butane and deodorized propane into an aerosol container to obtain a water-based aerosol preparation.

Pesticidal effects of the present compositions obtained in the above manner are as shown in the following examples:

EXAMPLE 1

According to the Campbell's turn table method ["Soap and Sanitary Chemicals"; Vol. 14, No. 6, page 119 (1938)], 5 ml. of each of the oil preparations obtained in Formulation Examples 1 and 2 was sprayed, and a group of about 100 housefly adults was exposed to the descending mist for 10 minutes. As the result, the death of more than 80 % of the flies could be observed on the next day.

EXAMPLE 2

The emulsifiable concentrate obtained in Formulation Example 3 was diluted with water to form a 20,000 times dilution. 2 Liters of the dilution was charged in a styrene case of 23 cm. in length, 30 cm. in width and 6 cm. in depth, and about 100 last-instar larvae of Northern house mosquitoes were liberated in the case. As the result, the death of more than 90 % of the larvae could be observed on the next day.

EXAMPLE 3

Rice plants, elapsed 45 days after sowing, were grown in 1/50,000 Wagner pots and sprayed with 10 ml/pot of an aqueous 200 fold dilution of each of the emulsifiable concentrates obtained in Formulation Example 3. Subsequently, each pot was covered with a wire net, and about 30 adults of green rice leafhoppers were liberated within the net. As the result, the death of more than 90 % of the leafhoppers could be observed on the next day.

EXAMPLE 4

In a glass Petri dish of 14 cm. in diameter were put 10 tobacco cutworm larvae at the third to fourth instar stage, and 1 ml. of an aqueous 200 times dilution of the emulsifiable concentrate obtained in Formulation Example 4 was sprayed to the larvae by use of a spraying tower. Subsequently, the larvae were transferred to another Petri dish with baits. As the result, the death of more than 90 % of the cutworm larvae could be observed after 2 days.

EXAMPLE 5

Pesticidal effects on housefly adults of the aerosol preparations obtained in Formulation Examples 5, 6, 7 and 16 were tested according to the aerosol test method [described in "Soap and Chemical Specialities"; Bluebook (1965)] using Peet Grady chamber (6 feet)³. As the result, all the aerosol preparation could knock down more than 80 % of the flies within 15 minutes after spraying and could kill more than 70 % of the flies on the next day.

EXAMPLE 6

About 50 adults of Northern house mosquitoes were released in a glass chamber of (70 cm.)³, and a small electric fan of 13 cm. in diameter equipped in the chamber was driven. Subsequently, 0.1 g. of each of the mosquito coils obtained in Formulation Examples 8 and 9 was ignited on both ends and put in the central part of the chamber bottom. As the result, more than 90 % of the mosquitoes could be knocked down within 20 minutes and the death of more than 80 % thereof could be ovserved on the next day.

EXAMPLE 7

About 50 adults of houseflies were released in a glass chamber of (70 cm.)³, and a small electric fan equipped in the chamber was driven. Subsequently, each of the heating fumigant compositions obtained in Formulation Examples 10 and 11 was placed on an electrically heated plate and fumigated in the chamber. As the result, more than 90 % of the houseflies could be knocked down within 20 minutes.

EXAMPLE 8

About 20 rice seedlings, grown in a flower pot of 9 cm. in diameter to the stage of 3 to 4 leaves, were sprayed on a turn table with an aqueous 200 fold dilution of each of the wettable powder preparations obtained in Formulation Example 12. After air-drying, each pot was covered with a wire cage, and then 20 to 30 adults of smaller brown planthoppers were liberated in the wire cage. After 24 hours, the number of alive and dead planthoppers was counted to find that more than 80 % of the insects had been killed.

EXAMPLE 9

Each of the dust preparations obtained in Formulation Example 13 was uniformly sprinkled on the bottom of a Petri dish of 14 cm. in diameter in the proportion of 2 g/m², and then butter was coated on the inner wall of the dish, except the portion of about 1 cm. from the bottom. Subsequently, a group of 10 adult German cockroaches was liberated in the dish and contacted with the dust preparation for 30 minutes, whereby more than 90 % of knocked down cockroaches could be killed during 3 days after the contact.

EXAMPLE 10

Into 10 liters of water in a 14 liter polyethylene-made pail was charged 1 g. of each of the granule preparations obtained in Formulation Examples 14 and 15. After one day, about 100 last-instar larvae of Northern house mosquitoes were liberated in said water, and the alive and dead of the larvae were observed with time. As the result, more than 90 % of the larvae could be killed within 24 hours.

EXAMPLE 11

Rice plants at the tillering stage were grown in 1/100,000 ares Wagner pots, and the depth of water was kept at 5 cm. Into the water in each pot, 10 kg/10 ares of each of the granule preparations obtained in Formulation Example 14 was charged. The pot was covered with a wire cage, and then adults of smaller brown planthoppers were released in the cage. After 24 hours, the death of more than 90 % of the planthoppers could be observed.

EXAMPLE 12

3 Grams of each of the oil preparations obtained in Formulation Example 2 was fogged by means of an insect fogger (manufactured by Burgess Vibrocrafters, Inc., U.S.A.) into the same Peet Grady chamber as in Example 5 into which about 500 houseflies had previously been liberated. As the result, more than 90 % of the houseflies could be knocked down within 30 minutes.

EXAMPLE 13

Chinese cabbages were grown in a green house, and were artificially parasitized with cutworms, cabbage worms and diamondback moths. Thereafter, the green house (2 m. in height) was divided into compartments of (30 m)² in area, and each compartment was fumigated, by use of a thermofumigator (SEARCH), with 10 g. of each of the wettable powder preparations obtained in Formulation Example 12. As a result, no increasing damage of the cabbages was substantially observed.

EXAMPLE 14

Mottled kidney bean plants (at the stage of 2 leaves), which had elapsed 9 days after sowing in flower pots, were parasitized with 10 to 15 carmine mites per leaf, and then allowed to stand for a week in a thremostat at 27°C., whereby the mites at various growth stages propagated in large numbers. At this stage, an aqueous 200 fold dilution of each of the emulsifiable concentrates obtained in Formulation Example 3 was sprayed to the plants in a proportion of 10 ml. per pot, using a turn table. After 10 days, the plants were observed to find almost no damage.

What is claimed is:

1. Cyclopropanecarboxylic acid esters represented by the formula,

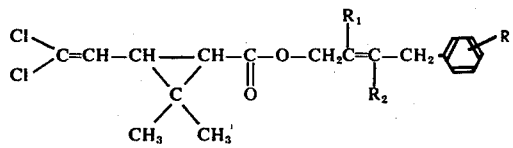

wherein R is a hydrogen atom, a halogen atom, a methyl or a methoxy group, and $R_1$ and $R_2$ are hydrogen atom, methyl group or a halogen atom.

2. A compound of the formula,

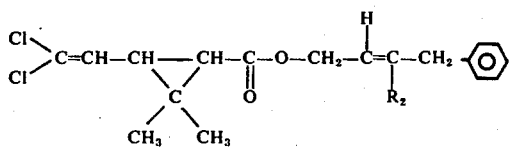

wherein $R_2$ is a hydrogen atom, a methyl group or a halogen atom.

3. A compound of the formula,

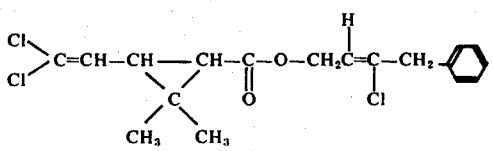

4. A compound of the formula,
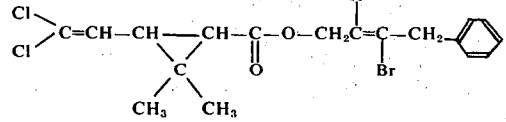
5. A compound of the formula,
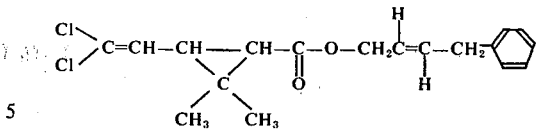
6. A compound of the formula,
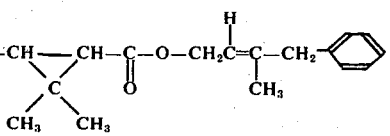
* * * * *